United States Patent
Bichler et al.

(10) Patent No.: US 11,547,588 B2
(45) Date of Patent: Jan. 10, 2023

(54) FOOT MOVEMENT DAMPING DEVICE AND SHOE FOR DAMPING A FOOT MOVEMENT VIA THE ANKLE JOINT

(71) Applicant: BETTERGUARDS TECHNOLOGY GmbH, Berlin (DE)

(72) Inventors: Vinzenz Bichler, Berlin (DE); Timo Stumper, Berlin (DE); Oscar Buschinger, Berlin (DE)

(73) Assignee: Betterguards Technology GmbH, Berlin (DE)

(*) Notice: Subject to any disclaimer, the term of this patent is extended or adjusted under 35 U.S.C. 154(b) by 295 days.

(21) Appl. No.: 16/612,207

(22) PCT Filed: May 8, 2018

(86) PCT No.: PCT/EP2018/061933
§ 371 (c)(1),
(2) Date: Nov. 8, 2019

(87) PCT Pub. No.: WO2018/206611
PCT Pub. Date: Nov. 15, 2018

(65) Prior Publication Data
US 2021/0137719 A1    May 13, 2021

(30) Foreign Application Priority Data
May 8, 2017  (DE) .................... 10 2017 109 877.1

(51) Int. Cl.
*A61F 5/01* (2006.01)
*A43B 7/20* (2006.01)
*A61F 5/058* (2006.01)

(52) U.S. Cl.
CPC .............. *A61F 5/0111* (2013.01); *A43B 7/20* (2013.01); *A61F 5/0127* (2013.01); *A61F 5/0585* (2013.01); *A61F 2005/0169* (2013.01)

(58) Field of Classification Search
CPC .... A61F 5/0111; A61F 5/0113; A61F 5/0127; A61F 5/0585; A61F 2005/0169; A43B 7/18; A43B 7/20
See application file for complete search history.

(56) References Cited

U.S. PATENT DOCUMENTS

| 3,527,209 A | 9/1970 | Baker |
| 3,613,273 A * | 10/1971 | Marquis .................. A43B 7/20 36/89 |

(Continued)

FOREIGN PATENT DOCUMENTS

| CN | 104510076 A | 4/2015 |
| CN | 104780798 A | 7/2015 |

(Continued)

OTHER PUBLICATIONS

International Search Report for corresponding International application PCT/EP2018/061933, dated Jul. 12, 2018, 5 pages.

(Continued)

*Primary Examiner* — Keri J Nelson
(74) *Attorney, Agent, or Firm* — Ruggiero, McAllister & McMahon LLC (57) ABSTRACT

A foot movement damper for damping a foot movement via the ankle joint, comprising a support arrangement for bearing on a lower leg and a holder arrangement for holding a foot, wherein a damping arrangement with at least one damping element is provided for damping a relative movement between the support arrangement and the holder arrangement, wherein the damping arrangement has a support binding for binding to the support arrangement and a holder binding for binding to the holder arrangement; and wherein the support arrangement has at least one bearing region and at least one bearing fixture, wherein the support arrangement can bear with the at least one bearing region over the malleolus of the ankle joint, and wherein the at least (Continued)

one bearing fixture is designed to fix the position of the at least one bearing region in a state when applied to the lower leg.

14 Claims, 4 Drawing Sheets

(56) References Cited

U.S. PATENT DOCUMENTS

| | | | | |
|---|---|---|---|---|
| 4,547,981 | A | * | 10/1985 | Thais ................ A43C 11/1493 36/89 |
| 4,577,419 | A | * | 3/1986 | Chassaing ................ A43B 5/00 36/89 |
| 4,982,733 | A | * | 1/1991 | Broadhurst ........... A61F 5/0111 602/27 |
| 5,382,224 | A | | 1/1995 | Spangler |
| 5,921,947 | A | * | 7/1999 | Kessler .................. A61F 13/64 602/27 |
| 9,668,534 | B2 | | 6/2017 | Normand |
| 9,675,490 | B2 | | 6/2017 | Maloney |
| 10,610,398 | B2 | * | 4/2020 | Benford ................ A61F 5/0127 |
| 2005/0177083 | A1 | * | 8/2005 | Heil ...................... A61F 5/0111 602/27 |
| 2006/0075661 | A1 | | 4/2006 | Ramsey |
| 2014/0223775 | A1 | | 8/2014 | Fleuren |
| 2015/0173926 | A1 | | 6/2015 | Bichler |
| 2017/0151082 | A1 | | 6/2017 | Bichler |

FOREIGN PATENT DOCUMENTS

| | | |
|---|---|---|
| DE | 102012011433 A1 | 11/2013 |
| DE | 102014107335 A1 | 1/2016 |
| DE | 102014113363 A1 | 3/2016 |
| DE | 102015107405 A1 | 11/2016 |
| EP | 0824014 A1 | 2/1998 |
| WO | 2012169895 A | 12/2012 |

OTHER PUBLICATIONS

Chinese Office Action for corresponding application 201880454814, 15 pages, dated May 8, 2021.
Chinese Search Report for corresponding application 201880454814, 4 pages, dated Apr. 26, 2021.
Canadian Office Action for corresponding application 3,062,715, 5 pages, dated Jul. 12, 2021.
Korean Office Action for corresponding application 10-2019-7036195, 14 pages, dated Oct. 11, 2021.

* cited by examiner

FOOT MOVEMENT DAMPING DEVICE AND SHOE FOR DAMPING A FOOT MOVEMENT VIA THE ANKLE JOINT

CROSS REFERENCE TO RELATED APPLICATIONS

The present application is a U.S. national stage patent application of International Patent Application No. PCT/EP2018/061933, filed on May 8, 2018, and claims foreign priority to German Patent Application No. 10 2017 109 877.1 filed on May 8, 2017, the entirety of each of which is incorporated by reference hereby.

FIELD OF THE DISCLOSURE

The present disclosure relates to a foot movement damping device for damping a foot movement via the ankle joint, and to a correspondingly configured shoe for damping a foot movement via the ankle joint.

DESCRIPTION OF THE RELATED ART

It is known to stabilize the movement of the ankle joint by means of devices for limiting foot movements, in order to counteract traumas caused by an ankle sprain, that is to say a movement of the ankle joint over at least one of its ankle joint axes in a non-physiological range. The most frequent form of sprain injury is an ankle joint distortion as stretching or tearing following an inversion. On account of the increasing inversion angle, inversion movements over an ankle joint axis result in a change of the distance between foot and lower leg. When a defined inversion angle or a defined inversion speed or inversion acceleration is exceeded, damage to the ligaments of the ankle joint or tears can occur.

To prevent this, devices are known which permit movements within a defined range and which, starting from a defined limit angle of the movement about the ankle joint axis, completely prevent movement. For this purpose, relatively rigid orthoses are known in which movements are inhibited mainly by use of splints or splint plates.

Moreover, devices are known in which a movement of the ankle joint is permitted as far as a defined limit angle of the movement and, on account of the structure, a movement is completely blocked starting from this limit angle. Such a device is known, for example, from EP 2717809 B1. Such devices provide no protective effect at all before the limit angle is reached. However, it is known that the risk of injury when twisting the ankle, particularly in the case of already weakened ligaments or after an injury, also depends significantly on the inversion speed and inversion acceleration occurring during twisting, and not only on the inversion angle. In the range below the limit (inversion) angle, such devices provide no protection at all. Moreover, after the limit angle is reached, a movement is completely blocked. The abrupt stopping of the twisting movement places a considerable load on the structure of the ankle joint, as a result of which there is an increased risk of injury, for example tearing at the bone or a cartilage injury. Moreover, on account of this blocking of the ankle joint, the twisting movement is transmitted to the next joint. In the case of a twisting of the ankle joint, this next joint is the knee joint. On account of the considerable lever arm present, the unfavorable introduction of force and the complexity of the knee joint, this can then lead to serious injuries, for example cruciate ligament tears or meniscal injuries, which, because of the way they restrict the person affected, and on account of their complexity and the relatively limited healing potential to healing, have much more negative consequences than an injury to the ankle joint ligaments.

Devices are also known which, when pulled on, always allow a minimum amount of movement but block dangerous movements. DE 10 2014 107 335 A1 discloses a device for adaptive limitation of an inversion movement via the ankle joint. In order to prevent the upper part of the orthosis from moving in the direction of the foot in the event of an action of force from the foot, the ankle joint orthosis disclosed therein requires a pressure-stable bar which is located on the medial side of the ankle joint and which extends between the upper region of the orthosis and the lower region of the orthosis and which has to be fixedly connected to both regions, in order to support the holding of the upper region. The bar has to be configured here in such a way that the tensile forces introduced into the upper region via the pull-out device on the lateral side are returned by it to the lower region as compressive forces on the medial side without deforming or buckling. This secures a position in the distal region. However, the bar on the medial side of the foot still limits the freedom of movement of the ankle joint.

SUMMARY

Proceeding from the known prior art, it is an object of the present disclosure to make available an improved foot movement damping device for damping a foot movement via the ankle joint.

The object is achieved by a foot movement damping device for damping a foot movement via the ankle joint having the features of claim 1. Advantageous developments emerge from the dependent claims, the description and the figures.

Accordingly, a foot movement damping device is proposed for damping a foot movement via the ankle joint, comprising a support arrangement for supporting on a lower leg and a retaining arrangement for retention on a foot. According to the disclosure, a damping arrangement is arranged with at least one damping element for damping a relative movement between the support arrangement and the retaining arrangement, wherein the damping arrangement has a support attachment for attaching to the support arrangement and a retaining attachment for attaching to the retaining arrangement. The support arrangement furthermore comprises at least one supporting region and at least one supporting fixation, wherein the support arrangement can be supported on the anklebone with the at least one supporting region above the anklebone of the ankle joint, and wherein the at least one supporting fixation is configured for fixing the position of the at least one supporting region in a state attached to the lower leg.

In the present case, the term "ankle joint" comprises the upper and the lower ankle joint and, accordingly, the movement axis of the upper ankle joint, which substantially permits the plantar flexion and dorsal extension of the foot, and the movement axis of the lower ankle joint, which substantially permits inversion and eversion, comprising supination, adduction and plantar flexion, abduction and dorsal extension.

Here, the term "anklebone" is understood as the eminence of the joint socket, the ankle mortise of the upper ankle joint. Consequently, the term "anklebone" in the present case comprises the lateral malleolus and the medial malleolus. By virtue of the configuration of the ankle mortise as joint socket, the anklebone has, with respect to the proximal-distal direction, a greater cross-sectional surface area compared to the above and consequently proximally adjoining portion of the lower leg. Therefore, the circumference of the anklebone is greater compared to the proximally adjoining portion.

Owing to the fact that a damping arrangement is provided with at least one damping element for damping a relative movement between the support arrangement and the retaining arrangement, wherein the damping arrangement has a support attachment for attaching to the support arrangement and a retaining attachment for attaching to the retaining arrangement, a movement even beyond a limit angle of the movement of the ankle joint can be provided. Moreover, the movement can be damped in each position of the foot.

Owing to the fact that the support arrangement comprises at least one supporting region and at least one supporting fixation, wherein the support arrangement can be supported on the anklebone with the at least one supporting region above the anklebone of the ankle joint, and wherein the at least one supporting fixation is configured for fixing the position of the at least one supporting region in a state attached to the lower leg, it is ensured that, in the event of an action of a tensile force on the support arrangement via the damping arrangement in the direction of the retaining arrangement, the force from the support arrangement can be transmitted via at least one supporting region thereof to the anklebone. In other words, when the foot movement damping device is fitted or pulled onto the user, the support arrangement is supported from above, that is to say proximally, in the direction of the foot, that is to say distally, on the anklebone in a substantially form-fitting manner. The form-fitting connection is made possible here by surrounding the tapered region of the lower leg proximally from the anklebone. Furthermore, it is therefore possible to configure the support arrangement in a flexible manner. A rigid arrangement with a hard shell which extensively covers the anklebone or the ankle joint is not necessary as a result.

The support fixation is configured here in such a manner that, when fitted or pulled on, it prevents the at least one supporting region from changing position with respect to the lower leg. The support fixation is preferably configured here as a band which is stiff in tension, preferably as a touch and close band, with a deflecting eyelet and a touch and close fastener, and therefore it can be pulled tightly on the lower leg via the deflecting eyelet and can be fixed by means of the touch and close fastener. This in particular prevents a radial expansion of the support arrangement such that the at least one supporting region cannot slip downward, i.e. distally, over the anklebone. Alternatively, the supporting fixation can also be provided as lacing on the support arrangement.

In particular by means of the combination of the abovementioned provision of the damping arrangement between support arrangement and retaining arrangement and the abovementioned configuration of the support arrangement, high mobility of the ankle joint during physiological movements that do not cause injuries and at the same time a good protective effect during non-physiological movement can thus be obtained in every position of the foot without the knee joint being unacceptably stressed during the damping of the twisting movement by the foot movement damping device. The at least one damping element can absorb a portion of the energy which arises during the twisting and which would otherwise have to be absorbed by the knee joint when the lever arm is increased. The at least one damping element is preferably set here in such a manner that a sufficiently large damping action is made available in order to avoid injuries to the ankle joint and, moreover, sufficient energy can be absorbed in order also to avoid injuries to the knee joint. In this way, the energy arising during the twisting is partially absorbed by the at least one damping element and is introduced via the support arrangement from above the anklebone via the upper region of the outer eminence of the ankle mortise into the lower leg, and is also partially compensated for by the knee joint.

In a preferred development, the support arrangement has flexible, pliant materials. The at least one supporting region is preferably formed by foam lying, in the pulled on state, against the lower leg in combination with a band which is stiff in tension, is arranged radially on the outside of the foam and runs in the circumferential direction of the lower leg. Said band preferably at the same time forms the supporting fixation. It is thereby possible to configure the support arrangement as a flexible foot restraint. The flexibility of the support arrangement makes it possible to avoid local pressure points or chafing points occurring on the anklebone. The at least one supporting region nestles against the surface of the upper side of the anklebone because of the flexible structure and thus uniformly distributes the pressure.

In a development, the support arrangement preferably has locally arranged, dimensionally stable or pressure-stable elements via which the force introduced into the support arrangement can be transmitted uniformly to the anklebone.

In a further preferred embodiment, the support arrangement has at least one first supporting region for supporting on a first side, preferably a lateral side of the ankle joint, and at least one second supporting region for supporting on a second side, preferably on a medial side of the ankle joint. The support arrangement can thereby be uniformly supported on the anklebone. Since the forces coming from the retaining arrangement via the damping arrangement are thereby transmitted distributed over the plurality of supporting regions into the anklebone and therefore a large force introduced on one side or locally is avoided, the support arrangement can be held particularly securely in its position. If the first supporting region is configured in such a manner that, in the fitted or pulled-on state, it is supported from above on the lateral malleolus, and the second supporting region is configured in such a manner that, in a fitted or pulled-on state, it is supported from above on the medial malleolus, particularly uniform support can be achieved.

In a preferred further embodiment, the support attachment is connected to the support arrangement at least partially on a first side of the support arrangement, which, in a state attached to the lower leg, preferably corresponds to a lateral side of the ankle joint, and at least partially on a second side of the support arrangement, which, in a state attached to the lower leg, preferably corresponds to a medial side of the ankle joint. By this means, in the event of an action of force coming from the retaining device, for example as a result of a twisting, the force is distributed to the first side of the support arrangement and to the second side of the support arrangement. Force components directed here in each case in the circumferential direction of the lower leg or of the support arrangement are thus introduced in a manner acting in opposite directions. The risk of slipping due to a force introduced or acting on one side in the circumferential direction is thereby reduced or even entirely avoided.

If, according to a further preferred embodiment, the support attachment has a first support arm for attaching to the support arrangement on the first side, and a second support arm for attaching to the support arrangement on the second side, the support attachment can be realized with a particular saving on material. Furthermore, according to the arrangement of the support arms, a force induced by a twisting can be diverted in a specific manner or introduced into the support arrangement in a manner acting in a preferred direction. Moreover, the anatomy of the foot or of the lower leg can thereby be taken into account and chafing points at exposed points can thereby be avoided.

In a particularly simple and robust embodiment, the first support arm and the second support arm are formed integrally.

According to a further preferred embodiment, a damping element is integrated in the first support arm and/or a damping element is integrated in the second support arm. The foot movement damping device can thereby be constructed particularly simply and compactly. If the support arms are arranged at an angle to the inversion direction or eversion direction of the ankle joint, a pull-out path of the respective damping element is extended in a manner corresponding to the angle enclosed between the respective support arm and the inversion direction or eversion direction. The damping behavior of the damping element can be set more precisely by the presence of correspondingly larger pull-out paths of the damping element. Moreover, a damping element which is integrated in a support arm has to absorb or to damp only the forces or force components which are transmitted through the respective support arm. The damping element can be constructed in a correspondingly smaller and simpler manner.

In a further preferred embodiment, a damping element is integrated in the retaining attachment. A direction of action of the damping element can thereby be precisely adapted to an anticipated inversion direction or can be predetermined in accordance therewith.

A particularly effective damping or restraint of the movement via the ankle joint can be achieved if the retaining attachment together with a plane defined by a sole or insert of the retaining arrangement encloses an angle of 0° to 90°, preferably of 30° to 70°, particularly preferably of 50° to 60° and very particularly preferably of 57°.

A "sole" is understood here to be a region which, when the device is pulled on, is in flat contact with at least part of the foot lower side of the wearer. The sole is preferably configured as an insert.

In a preferred further embodiment, the device is made available as a completely separate device. In other words, the device functions without having to be combined with other devices. In particular, parts of the device do not need to be fastened to a shoe or integrated therein.

In order to be able to particularly effectively damp the ankle joint movement by means of the foot movement damping device, according to a further preferred embodiment the retaining attachment or the damping element integrated in the retaining attachment is arranged in such a manner that, as seen in a side view of the foot movement damping device, that is to say a medial view or lateral view of a foot of a person wearing the foot movement damping device, the resulting direction of action or resulting line of action of the damping element intersects the sole of the retaining region approximately in a region of metatarsophalangeal joint D5 of the foot, that is to say in the region between the metatarsal bone and the proximal phalanx of the little toe of the foot.

So that the mobility of the foot wearing the foot movement damping device device is influenced only to a small extent, according to a further preferred embodiment a transition between the support attachment and the retaining attachment is configured in an articulated or movable manner. The transition is preferably configured in the form of a sliding joint, a rotary joint or a transverse force joint. Alternatively, the transition can be configured as a deflection, wherein the transition then preferably has a roller, an eyelet and/or a loop. For example, in the event of a plantar flexion or dorsal extension of the foot wearing the foot movement damping device, the support attachment can thus be rolled or moved relative to the retaining attachment in the region of the transition without the range of the aforementioned movement being restricted by the foot movement damping device.

In a further preferred embodiment, the foot movement damping device is arranged on a sock, a football sock, an orthosis or a bandage.

In a further preferred embodiment, at least one of the support arms has an adjustable attachment region for adapting a length of the support attachment. The adjustable arrangement is preferably configured in the form of a latching arrangement, a hook connection or a touch and close connection. The adjustable attachment region is preferably fixed by the fitting of the supporting fixation.

The abovementioned object is furthermore achieved by a shoe for damping a foot movement via the ankle joint, with the features of claim 10. Advantageous developments emerge from the dependent claims, the description and the figures.

Accordingly, a shoe for damping a foot movement via the ankle joint is proposed, which comprises a sole and an upper. According to the disclosure, a foot movement damping device according to one of the preceding embodiments is arranged on the shoe. Owing to a foot movement damping device according to one of the preceding embodiments being provided on the shoe, a user or wearer of the shoe can benefit from the above-described advantages.

A "shoe" is understood here as any form of shoe-like foot apparel with an upper or shoe shaft and, connected to the latter, a solid base or sole, in particular orthopedic shoes, sports shoes, leisure shoes and boots.

In a further preferred embodiment of the shoe, the damping arrangement is at least partly arranged on an outer side of the shoe. The paths resulting in the event of a twisting, in particular the resulting pull-out path, are thereby as large as possible, which permits a particularly precise adjustment of the damping arrangement and particularly effective damping. Furthermore, a shoe can easily be retrofitted with the foot movement damping device and parts can be easily maintained and/or exchanged.

In a further preferred embodiment of the shoe, the retaining attachment is at least partially integrated in the shoe and/or the support attachment is at least partially integrated in the shoe and/or at least one damping element is integrated in the shoe, wherein preferably the entire damping arrangement is integrated in the shoe. A particularly stiff and compact construction of the shoe can thereby be achieved. Furthermore, the shoe can then be configured in such a manner that fewer or no parts which, during use of the shoe, for example during soccer games, have an adverse effect on practising the sport, protrude on the outer side of the shoe. In addition, the shoe can be configured in such a manner that it differs only insignificantly, if at all, from a shoe which does not have a foot movement damping device for damping purposes, as viewed from the outside. The esthetic appearance of the shoe can therefore be very substantially maintained in relation to that of a conventional shoe.

In a further preferred embodiment of the shoe, the support arrangement is made available as a separate component. "Made available separately" should be understood here as meaning that the support arrangement is connected to the shoe only via the support attachment or the damping arrangement. The shoe can thereby be configured substantially corresponding to a shoe which does not have a foot movement damping device for damping purposes. The separate support arrangement is then a component which is not connected to the textile material of the shoe. The sole connection between the actual shoe and the support arrangement is accordingly the support attachment. In particular in shoes having a low shaft, such as running shoes or soccer shoes, maximum mobility of the foot can thus be achieved.

In a particularly preferred further embodiment, the shoe has a high shaft, wherein the support arrangement is integrated in the high shaft. Separate provision of the support arrangement is thereby unnecessary. Moreover, movement of the support arrangement is thereby substantially prevented. The supporting fixation is preferably arranged on the outer side of the shoe in the form of a loop, band or sling with an eyeletlet. Alternatively, the supporting fixation can also be configured by regions of the shaft and of a primary closing device of the shoe, for example lacing of a laced shoe or a touch and close fastener of a touch and close fastener shoe, that are stiff in tension.

BRIEF DESCRIPTION OF THE FIGURES

Preferred further embodiments will be explained in more detail by the description below of the figures, in which.

DETAILED DESCRIPTION OF PREFERRED EXEMPLARY EMBODIMENTS

Preferred exemplary embodiments will be described below with reference to the figures. Elements that are identical or similar or that have an identical action are provided with identical reference signs in the different figures. A repeated description of these elements is dispensed with to some extent in order to avoid redundancy.

Figure 1:
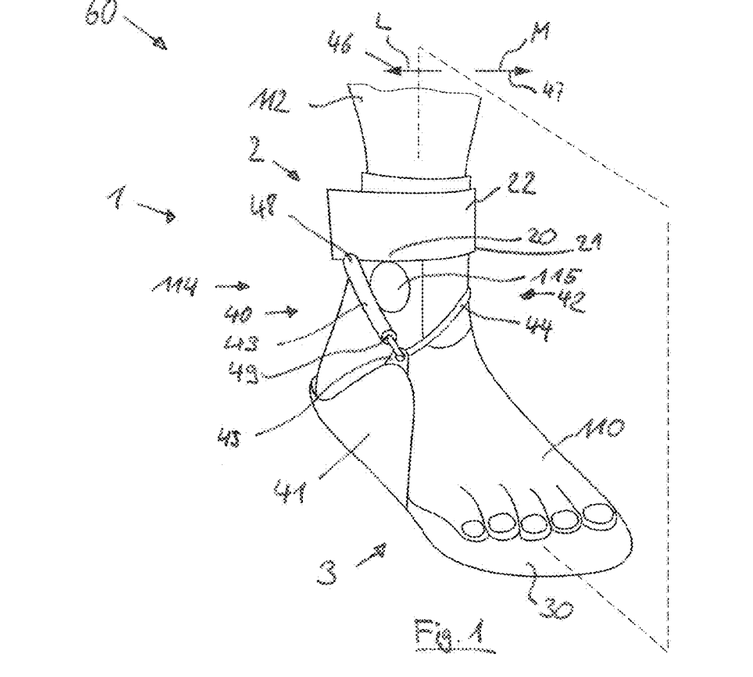
FIG. 1 shows a schematic perspective side view of a foot movement damping device for damping a foot movement via the ankle joint, according to a first embodiment.

FIG. 1 shows a schematic perspective side view of a foot movement damping device 1 for damping a foot movement via the ankle joint, according to a first embodiment, which is attached to a human foot 110. The foot movement damping device 1 is in the form of an orthosis 60. The foot movement damping device 1 is attached to the foot 110 below the anklebone 114, the ankle mortise, of the ankle joint of the foot 110 via a retaining arrangement 3. Above the anklebone 114, the foot movement damping device 1 is attached to a lower leg 112 by means of a support arrangement 2. The support arrangement 2 and the retaining arrangement 3 are connected via a damping arrangement 4 which damps a relative movement between the support arrangement 2 and the retaining arrangement 3 adaptively, here in a speed-dependent manner and in an acceleration-dependent manner. The foot movement damping device 1 according to FIG. 1 is configured here in such a manner that it can adaptively damp an inversion movement of the ankle joint.

For the attachment to the foot 110, the retaining arrangement 3 has a sole 30 on which the sole of the foot 110 rests. The sole 30 is connected on a first side 46 of the foot movement damping device 1, which side corresponds here to the lateral side L of the foot 110, to a retaining attachment 41 of the damping arrangement 4. The retaining attachment 41 is connected to a support attachment 42 of the damping arrangement 4 by means of a transition 45, here in the form of an eyeletlet attached to the retaining attachment 41. Via the support attachment 42 in turn, the damping arrangement 4 is connected to the support arrangement 2. The support attachment 42 is formed in one piece in the form of a band which is stiff in tension and is deflected in the eyeletlet of the transition 45. The support attachment 42 is thereby divided into a first and a second support arm 43, 44. The first support arm 43 extends on the first side 46 of the foot movement damping device 1 or of the support arrangement 2 between the transition 45 and the support arrangement 2. The second support arm 44 extends from the transition 45, which is located on the first side 46, to the second side 47 of the foot movement damping device 1 or of the support arrangement 2 and is connected there to the support arrangement 2. The support attachment 42 or the band is guided movably in the transition 45. During a plantar flexion or a dorsal extension over the ankle joint (or over the upper ankle joint axis thereof), the section on which the band of the support attachment 42 is deflected in the eyeletlet is moved in accordance with the range of the movement. The lengths of the first support arm 43 and of the second support arm 44 thereby change slightly. This slight change is compensated for by slight sliding of the band in the eyeletlet, and therefore, when attached firmly, possible wrinkles or pressure points arising on the skin are avoided.

If the ankle joint undergoes an inversion, the distance between retaining arrangement 3 and support arrangement 2 increases on the first side 46. Consequently, the distance between the support arrangement 4 and the transition 45 increases. Accordingly, an extension to the length of the support attachment 42 from a first attachment region on the support arrangement 2 on the first side 46 via the eyeletlet of the transition 45 and to a second attachment region on the support arrangement 2 on the second side 47 would be necessary. In order basically to permit such a movement in the physiological range, the damping arrangement 4 has a damping element 40 which is integrated in the first support arm 43. The damping element 4 has a tubular first damper part 48, which is connected fixedly to the support arrangement 2, and has a second damper part 49, which is movable relative to the first damper part 48 along a pull-out direction extending along the longitudinal axis of the tubular first damper part 48 and is connected to the band of the support attachment 42. The second damper part 49 partially extends in the interior of the tubular first damper part 48 and has a pull-out body therein. Furthermore, a damping medium is contained in the damping element. During a relative movement of the second damper part 49 in relation to the first damper part 48, the movement of the second damper part 49 is damped in accordance with the geometry of the inner side of the first damper part 48 and of the pull-out body of the second damper part 49 and the composition, in particular the viscosity, of the damping medium. The damping element 40 is configured here in such a manner that it adaptively damps the movement. During movements of moderate speeds or accelerations, a virtually unimpeded mobility of the ankle joint can thus be made available. If an inversion occurs at high speeds and/or accelerations at which there is a risk of injury to the ligaments of the ankle joint, the damping element 40 damps the inversion movement and injury is avoided.

The damping element 40 furthermore has a seal for sealing the interior of the first damper part 48, which has the damping medium, and a resetting means for resetting the second damper part 49 into a position retracted or pushed into the first damper part 48. The resetting means ensures that the second damper part 49 is moved back into the first damper part 48 when the foot is moved back from an inversion position. The protective effect of the foot movement damping device 1 is thereby available not only when or after a defined limit inversion angle is reached, but rather in substantially every position of the foot.

So that the support arrangement 2 does not move during an action of force as a result of an inversion, in particular does not slip downward in the direction of the foot 110, the support arrangement 2 has a first and a second supporting region 20, 21. The first supporting region 20 is arranged on the first side 46 of the support arrangement 2 such that, when the foot movement damping device 1 is attached to the foot 110 or lower leg 112, said first supporting region is located substantially above the lateral malleolus 115. Opposite, i.e. on the second side 47, the support arrangement 2 has a second supporting region 21 (not shown here). The second supporting region 21 is arranged here on the support arrangement 2 in such a manner that, when the foot movement damping device 1 is attached to the foot 110 or lower leg 112, said second supporting region is located substantially above the medial malleolus. In the event of an inversion, in which a tensile force in the direction of the foot 110 is introduced into the support arrangement 2 via the support attachment 42, the support arrangement 2 is supported on the lateral malleolus 115 of the ankle joint from above with the first supporting region 20 and on the medial malleolus of the ankle joint from above with the second supporting region 21. In order to prevent the support arrangement 2 from expanding radially and the supporting regions 20, 21 from thus slipping downward over the anklebone 114 in the direction of the foot 110, the support arrangement 2 has a supporting fixation 22 by means of which the position of the first supporting region 20 and of the second supporting region 21 is fixed on the lower leg. The supporting fixation 22 is designed here as a touch and close band 25 with a deflecting eyeletlet and a touch and close fastener, and therefore it can be tautly pulled on the lower leg 112 via the deflecting eyeletlet and fixed by means of the touch and close fastener.

The foot movement damping device 1 from FIG. 1 is configured as a completely separate device which deploys its protective effect because of its structure. A person wearing the device 1 does not have to pull a shoe over the device 1 in order to obtain the abovementioned protective effect. However, the device 1 can be configured in such a manner that wearing of the device 1 under or in a shoe is possible without pressure points occurring on the foot. For this purpose, the sole 30 can preferably be configured as an insert which replaces an insert in a shoe or can be placed on said insert.

Figure 2:
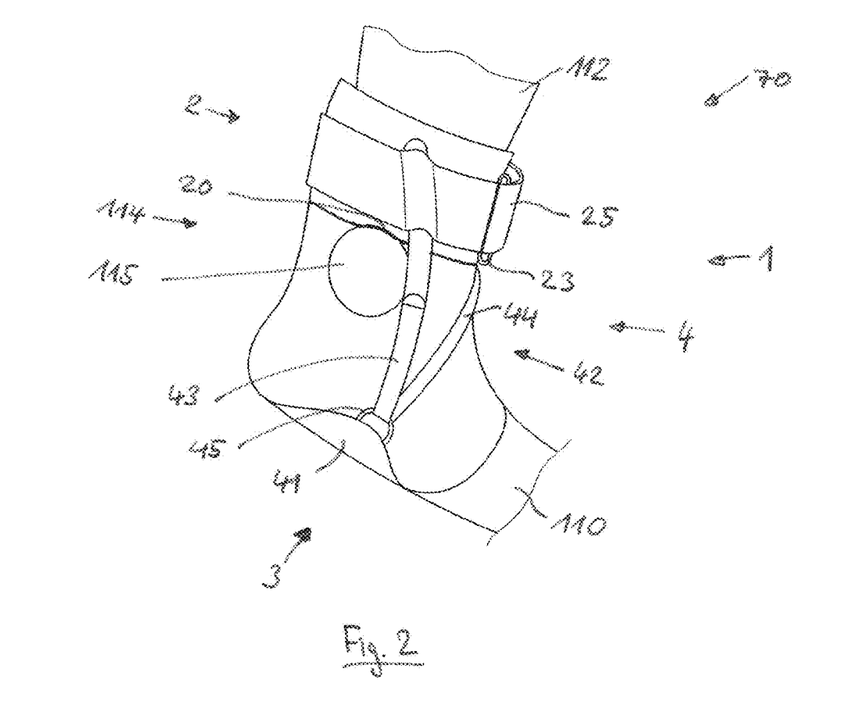
FIG. 2 shows a schematic side view of a foot movement damping device device for damping a foot movement via the ankle joint, according to a further embodiment.

FIG. 2 shows a schematic side view from a first side 46, the lateral side of the ankle joint, of a foot movement damping device 1 for damping a foot movement via the ankle joint, according to a further embodiment in which the foot movement damping device 1 is provided on a bandage 70. The bandage 70 has, as the main structure, a stocking 72 made from an elastic compression knit which can be adapted to the wearer's body.

The support arrangement 2 is arranged on the stocking 72 of the bandage 70 in such a manner that it is located above the anklebone 114 when the bandage 70 is attached to the foot 110 and lower leg 112. According to the embodiment from FIG. 1, the support arrangement 2 has a first supporting region 20 for supporting on the lateral malleolus 115 and a second supporting region 21 (not shown) for supporting on the medial malleolus. On the lower side of the bandage 70, the latter has a retaining arrangement 3 which is stiff in tension and which is connected laterally to a retaining attachment 41 designed as a small fabric tab. A transition 45 in the form of a loop is arranged on the retaining attachment 41. Via the loop, the support attachment 42, which is configured as a band which is stiff in tension according to the embodiment of the foot movement damping device 1 from FIG. 1, is deflected coming from a first attachment region 43a, located on the first side 46, on the support arrangement 2 in the direction of a second attachment region 44a (not shown) located on the second side 47. Consequently, the support attachment 42 in turn is divided into a first support arm 43 for attachment to the support arrangement 2 on the first side 46 and a second support arm 44 for attachment to the support arrangement 2 on the second side 47.

The damping element 40 is arranged here in the attachment region 43a and extends substantially over the entire width of the touch and close band 25 of the support arrangement 2. As a result, the bandage 70 does not have any pronounced eminences below the anklebone 114. The bandage 70 is therefore particularly suitable for being worn below a low-shaft shoe without pressure points being formed on the foot due to possible eminences.

Figure 3:
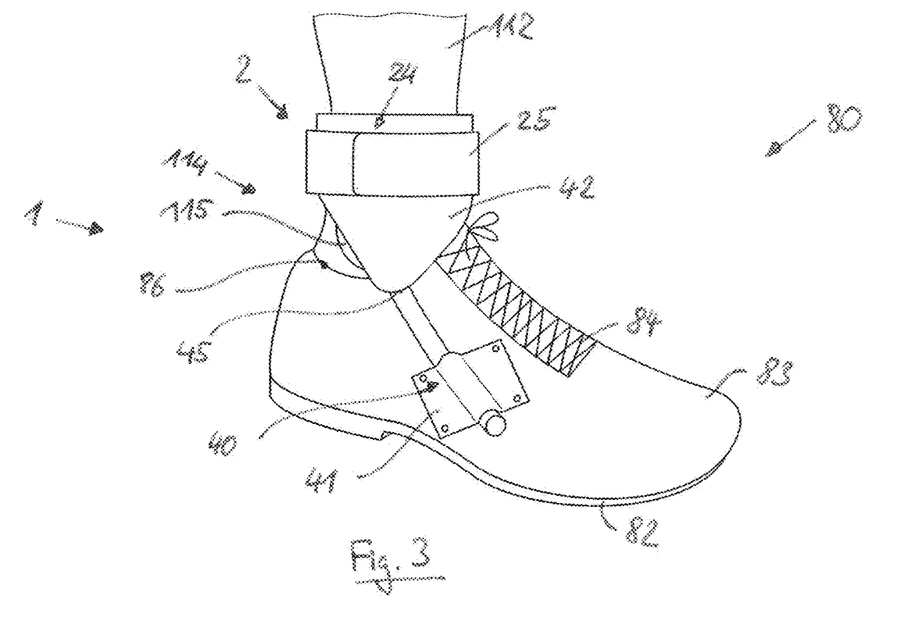
FIG. 3 shows a schematic side view of a low-shaft shoe for damping a foot movement via the ankle joint, according to a first embodiment.

FIG. 3 shows a schematic side view from the first side 46 of a low-shaft shoe 80 for damping a foot movement via the ankle joint, according to a first embodiment. A foot movement damping device 1 for damping a foot movement via the ankle joint is provided on the shoe 80. The shoe 80 is configured as a laced sports shoe with a shoe sole 82 and an upper, the shoe shaft 83, the shaft end 86 of which, in the pulled-ontate, is arranged below the anklebone 114. The shoe shaft 83 does not extend over the anklebone 114.

The retaining arrangement 3 is formed by the shoe sole 82 and the upper, that is to say the shoe shaft 83. The positionally stable attachment to the foot 110 is achieved by means of the lacing 84, by means of which the shoe shaft 83 can be pulled onto the contour of the foot 110. On the first side 46, that is to say the lateral side of the foot 110, a retaining connection 41 in the form of a dimensionally stable flange is fastened to the shoe shaft 83. A damping element 40 is fastened to the flange. The damping element 40 is fixedly connected to the transition 45 by a support attachment 42 in the form of a knitted fabric which is stiff in tension. The support attachment 42 is connected to the support arrangement 2 by a part on the first side 46 of the support arrangement 2, which side, in the state of attachment to the lower leg 112, corresponds to a lateral side of the ankle joint, and by a further part on a second side 47 of the support arrangement 2, which side, in the state of attachment to the lower leg 112, corresponds to a medial side of the ankle joint. Forces introduced by the damping arrangement 4 into the support arrangement 2 via the support attachment 41 are therefore introduced into the support arrangement 2 both on the first side 46 and on the second side 47.

Figure 4:
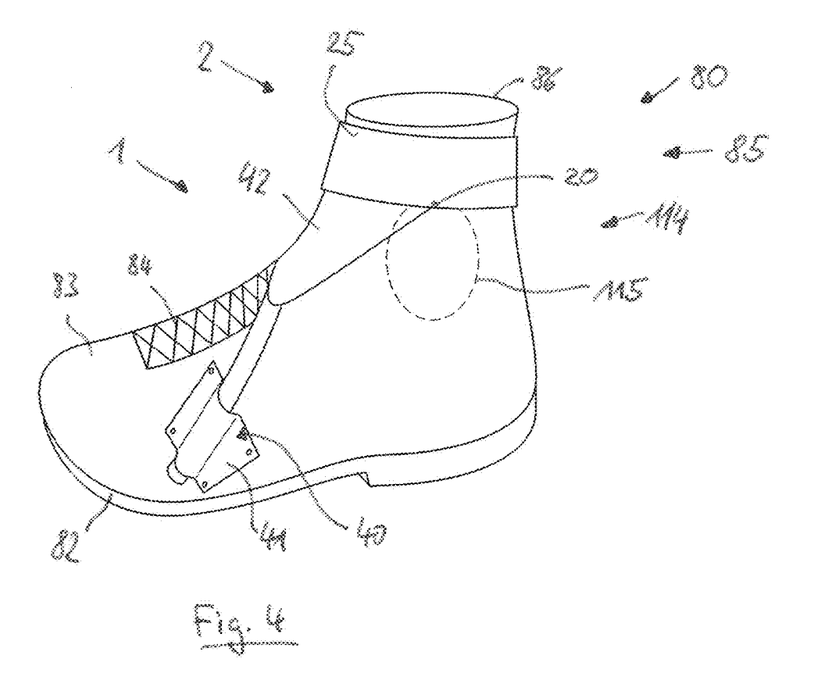
FIG. 4 shows a schematic side view of a high-shaft shoe for damping a foot movement via the ankle joint, according to a further embodiment.

In the embodiment shown in FIG. 4, the support arrangement 2 is configured as a separate component. Consequently, the support arrangement 2 is connected to the shoe shaft 83 only via the support attachment 42 of the damping arrangement 4. In the pulled-on state, there is therefore a distance between the support arrangement 2 arranged above the anklebone 114 and the shaft end 86 located below the anklebone 114.

FIG. 4 shows a schematic side view of a high-shaft shoe 80 with a foot movement damping device 1 for damping a foot movement via the ankle joint. The basic construction of the shoe 80 substantially corresponds to that of the shoe from FIG. 3, but it differs in that the shoe 80 from FIG. 4 has a high shaft 85. The shaft end 86 of the shoe 80, in the pulled-on state, therefore lies above the anklebone 114, which is indicated here by the reference sign 114. Furthermore, the support arrangement 2 is integrated in the shoe 80. The support arrangement 2 has a first supporting region 20 for supporting from above on the lateral malleolus 115 on the first side 46 and a second supporting region 21 (concealed here) for supporting from above on the medial malleolus 116 (not shown) on the second side 47. The supporting regions 20, 21 are arranged in the interior of the high shaft 85. In order to ensure the stability of the support arrangement 2, a supporting fixation 22 in the form of a touch and close band 25 is provided on the high shaft 85.

Figure 5:
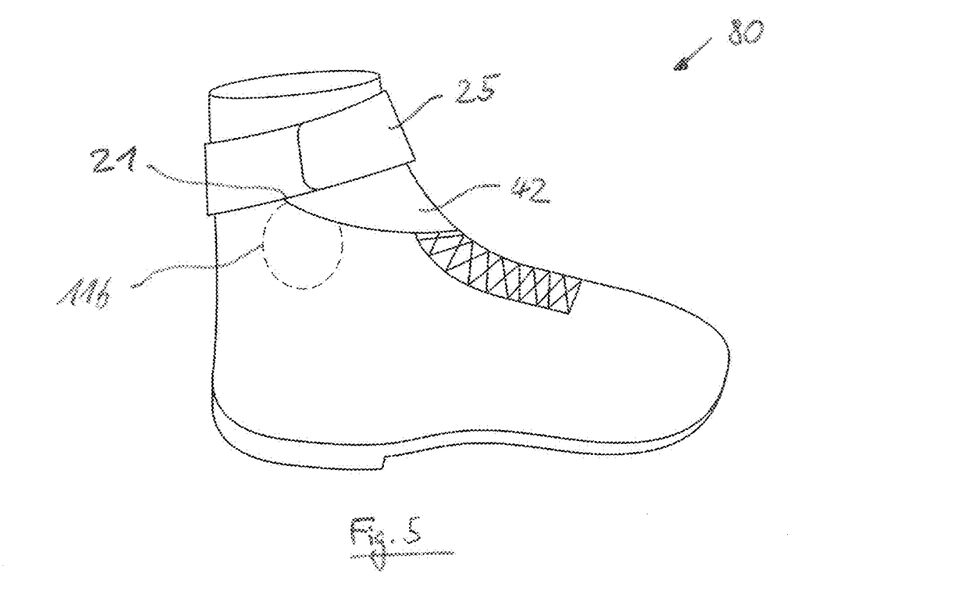
FIG. 5 shows schematically the shoe from FIG. 4, as seen from a different side.

FIG. 5 shows schematically the shoe 80 from FIG. 4 as seen from the second side 47, the medial side of the ankle joint. The support attachment 42 extends on the second side 47 approximately as far as the rear end of the position of the medial malleolus that is indicated here by the reference sign 116.

Figure 6:
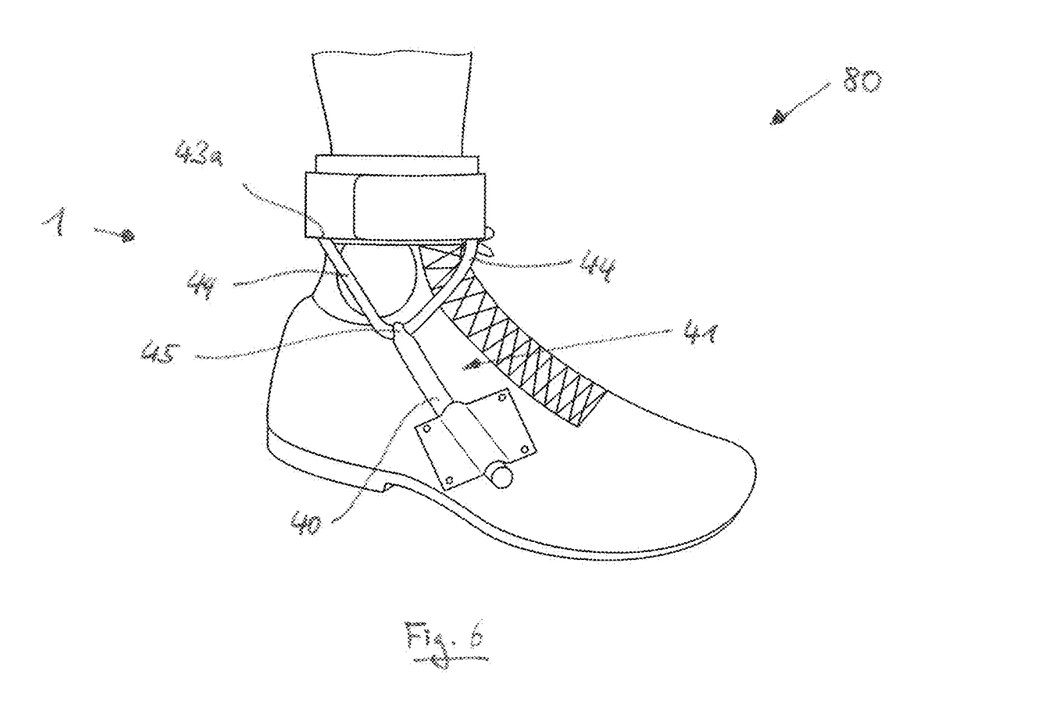
FIG. 6 shows a schematic side view of a low-shaft shoe for damping a foot movement via the ankle joint, according to a further embodiment.

FIG. 6 shows a schematic side view of a low-shaft shoe 80 with a foot movement damping device 1 for damping a foot movement via the ankle joint, according to a further embodiment. The shoe 80 very substantially corresponds to that from FIG. 3. The sole difference is that the shoe 80 shown in FIG. 6 has, instead of the flat knitted fabric, a support attachment 42 in the form of a band which is stiff in tension and which is divided by the transition 45 to the retaining attachment 41 into a first support arm 43 and a second support arm 44. The first support arm 43 is connected to the support arrangement 2 at a first attachment region 43a located on the first side 46 and is connected to the support arrangement 2 at a second attachment region 44a (not shown) located on the second side 47. The transition 45 is configured as a fixed seam.

Figure 7:
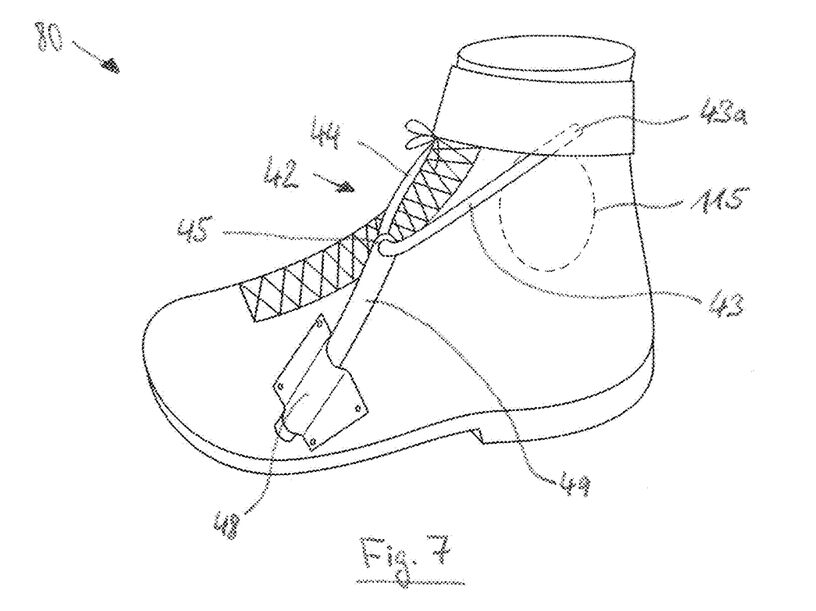
FIG. 7 shows a schematic side view of a high-shaft shoe for damping a foot movement via the ankle joint, according to a further embodiment.

FIG. 7 shows a schematic side view of a high-shaft shoe 80 with a foot movement damping device 1 for damping a foot movement via the ankle joint, according to a further embodiment. The high-shaft shoe 80 corresponds to that from FIG. 4, wherein, instead of the flat knitted fabric, the support attachment 42 is made available in the form of a lace which is stiff in tension, which has a substantially round cross section and which is divided by the transition 45 to the retaining attachment 41 into a first support arm 43 and a second support arm 44. The first support arm 43 is connected to the support arrangement 2 at a first attachment region 43a located on the first side 46 and is connected to the support arrangement 2 at a second attachment region 44a (not shown) located on the second side 47. The transition 45 is configured as an eyeletlet at the end of the second damper part 46, in which eyeletlet the lace is movably held.

Figure 8:
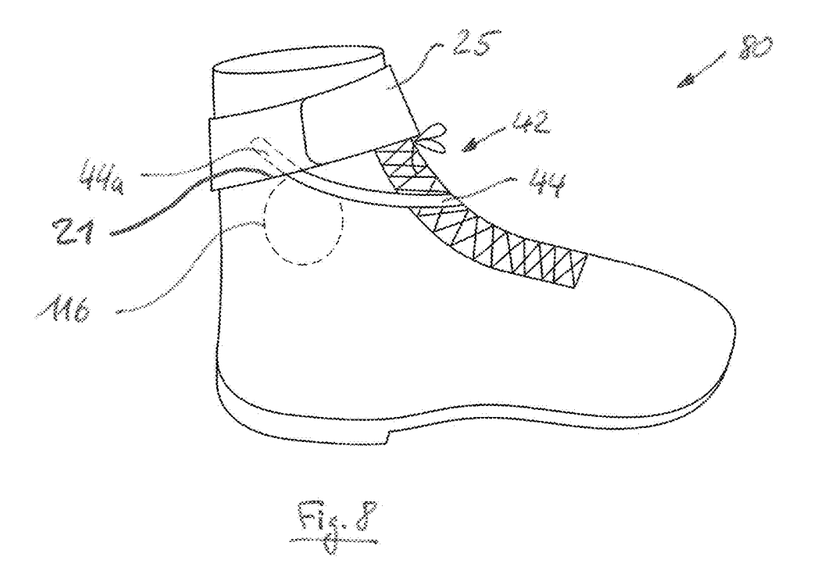
FIG. 8 shows schematically the shoe from FIG. 7, as seen from a different side.

FIG. 8 shows schematically the shoe 80 from FIG. 7 as seen from the second side 47, the medial side of the ankle joint. The support attachment 42 extends on the second side 47 approximately as far as the rear end of the position of the medial malleolus that is indicated here by the reference sign 116. Furthermore, the second attachment region arranged below the touch and close band is indicated by the reference sign 44a.

Instead of a rigid attachment, in the abovementioned embodiments, the first attachment region 43a and/or the second attachment region 44a can be configured to be adjustable. For example, at least one of the support arms 43, 44 can have a latching arrangement, a hook connection with a plurality of hooks arranged in a row on the support attachment, or a touch and close connection. The at least one adjustable attachment region 43a, 44a is preferably additionally fixed by the fitting of the support fixation 22.

Where applicable, all the individual features set out in the exemplary embodiments can be combined with one another and/or interchanged, without departing from the scope of the invention.

LIST OF REFERENCE SIGNS

1 Foot movement damping device
2 Support arrangement
20 Supporting region
22 Supporting fixation
23 Deflecting eyeletlet
24 Touch and close fastener
25 Touch and close band
3 Retaining arrangement
30 Sole
4 Damping arrangement
40 Damping arrangement
41 Retaining attachment
42 Support attachment
43 First support arm
43a First attachment region
44 Second support arm
44a Second attachment region
45 Transition
46 First side
47 Second side
48 First damper part
49 Second damper part
60 Orthosis
70 Bandage
72 Stocking
80 Shoe
82 Shoe sole
83 Shoe shaft
84 Lacing
85 High shaft
86 Shaft end
110 Foot
112 Lower leg
114 Anklebone
115 Lateral malleolus
116 Medial malleolus
N Medial side
L Lateral side

The invention claimed is:

1. A foot movement damping device for damping a foot movement via the ankle joint, comprising a support arrangement for supporting on a lower leg and a retaining arrangement for retention on a foot, wherein a damping arrangement is arranged with at least one damping element for damping a relative movement between the support arrangement and the retaining arrangement, wherein the damping arrangement has a support attachment for attaching to the support arrangement and a retaining attachment for attaching to the retaining arrangement; and in that the support arrangement comprises at least one supporting region and at least one supporting fixation, wherein the support arrangement is configured to be supported on the anklebone with the at least one supporting region above and not over the anklebone of the ankle joint, and wherein the at least one supporting fixation is configured for fixing the position of the at least one supporting region in a state attached to the lower leg.

2. The foot movement damping device as claimed in claim 1, wherein the at least one support region of the support arrangement comprises at least one first supporting region for supporting on a first side of the ankle joint, and at least one second supporting region for supporting on a second side of the ankle joint.

3. The foot movement damping device as claimed in claim 1 wherein the support attachment is connected to the support arrangement at least partially on a first side of the support arrangement, which, in a state attached to the lower leg, corresponds to a lateral side of the ankle joint, and at least partially on a second side of the support arrangement, which, in a state attached to the lower leg, corresponds to a medial side of the ankle joint.

4. The foot movement damping device as claimed in claim 3, wherein the support attachment has a first support arm for attaching to the support arrangement on the first side, and a second support arm for attaching to the support arrangement on the second side.

5. The foot movement damping device as claimed in claim 4, wherein the first support arm and the second support arm are formed integrally.

6. The foot movement damping device as claimed in claim 4 wherein the at least one damping element is integrated in the first support arm and/or the at least one damping element is integrated in the second support arm.

7. The foot movement damping device as claimed in claim 1, wherein the at least one damping element is integrated in the retaining attachment.

8. The foot movement damping device as claimed claim 1, wherein a transition between the support attachment and the retaining attachment is configured in an articulated or movable manner.

9. A shoe for damping a foot movement via the ankle joint, comprising a sole and a top part, wherein the shoe has a foot movement damping device as claimed in claim 1.

10. The shoe as claimed in claim 9, wherein the damping arrangement is at least partially arranged on an outer side of the shoe.

11. The shoe as claimed in claim 9, wherein the retaining attachment is at least partially integrated in the shoe and/or the support attachment is at least partially integrated in the shoe and/or at least one damping element is integrated in the shoe.

12. The shoe as claimed in claim 9, wherein the support arrangement is provided as a separate component.

13. The shoe as claimed in claim 9, wherein the shoe has a high shaft, wherein the support arrangement is integrated in the high shaft.

14. The shoe as claimed in claim 9, wherein the entire damping arrangement is integrated in the shoe.

* * * * *